Sept. 20, 1938. F. C. STIELOW Plant Pat. 292
ROSE
Filed May 28, 1937
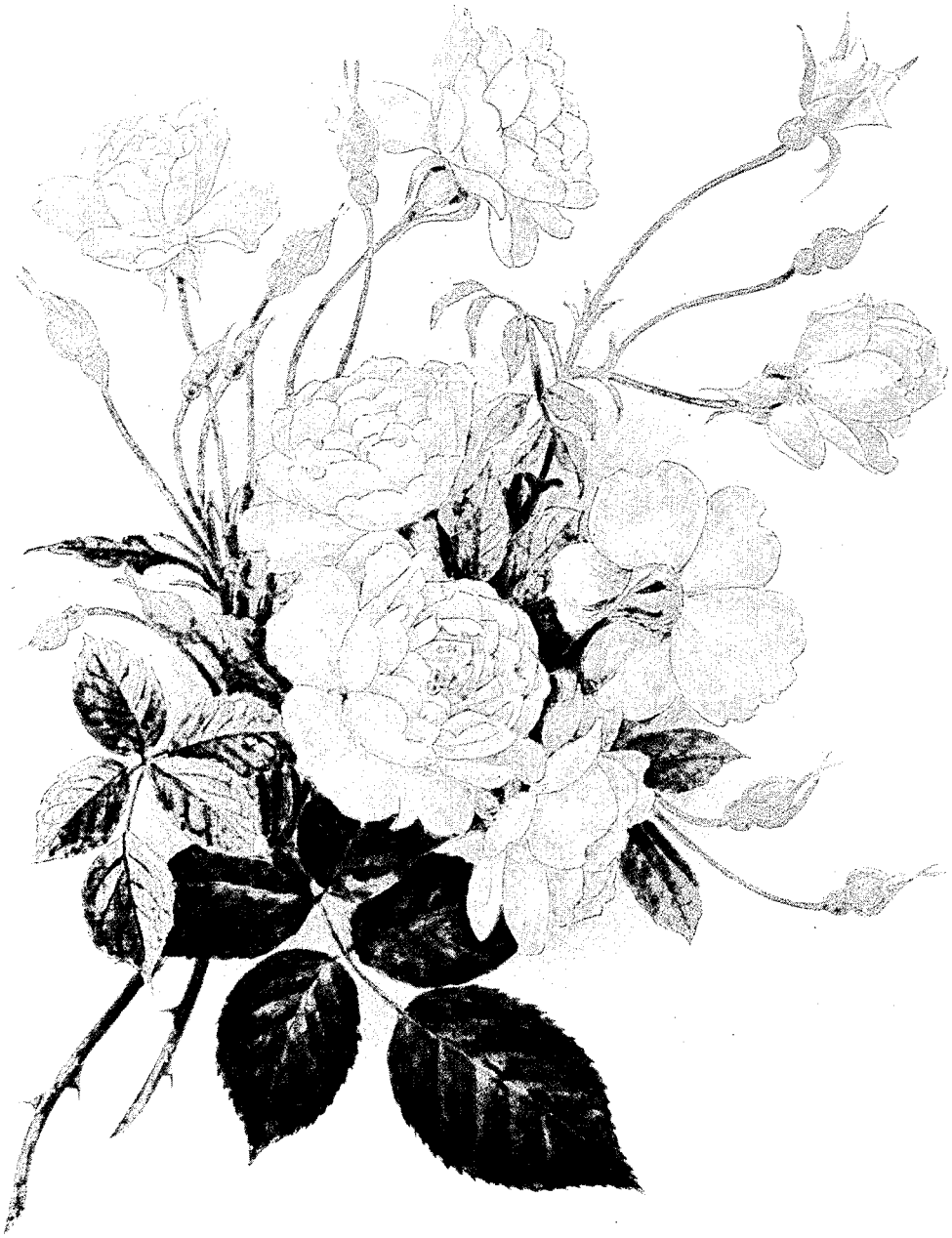
Witness,
Addison E. Avery
Inventor,
Fred C. Stielow
by
Rummler, Rummler
& Woodworth Patented Sept. 20, 1938

Plant Pat. 292

UNITED STATES PATENT OFFICE

292

ROSE

Fred C. Stielow, Niles Center, Ill.

Application May 28, 1937, Serial No. 145,321

1 Claim. (Cl. 47—61)

The new variety of rose herein described and illustrated is a sport of the rose known in the United States as "Mrs. Finch",—an Australian rose,—which was purchased from A. N. Pierson, Inc., of Cromwell, Conn. This sport was propagated by me at my greenhouses in Niles Center, Illinois, and has been asexually reproduced.

The discovery of the new rose makes possible the production of a rose which is a more continuous bloomer than the parent, which has a deeper shade of pink, and which retains the deep color for a comparatively long period without fading. The new rose is desirable for corsage bouquets. The parent plant "Mrs. Finch" is noticeably subject to fading and is less vigorous than the new plant.

The new rose is distinguishable from the parent rose by its deeper pink blossoms and more permanent color retention, and its somewhat more double and more cup-shape than the blossoms of the "Mrs. Finch" rose. The new plant grows vigorously, blossoms freely and continuously and the cut flowers have long-lasting qualities. The petals adhere well for two or three weeks on the cut flower. The plant has been produced in quantity by budding and grafting since January, 1937; and remains true to form and color and free from disease.

The favorable results of this discovery are a "Mrs. Finch" rose with a desired increase in color depth and less fading in warm weather.

The accompanying illustration shows in full color a composition of two typical sprays of the plant as having several buds, some of which are partly open and others in full bloom.

The rose has a desirable color, is a free and continuous bloomer and the flowers keep well. Like the original "Mrs. Finch" rose the modified one is used to a considerable extent in making up corsage bouquets. The new plant has been asexually reproduced and the distinctive characteristics herein set forth are maintained true to form and appear to be permanently fixed. When the blossoms are fully open some of the petals have whitish pink areas near the base.

The colors of this rose in detail and with exactness are as follows, reference being made to Maerz & Paul's Color Dictionary:

| Section | Color | Plate | Letter | No. |
|---|---|---|---|---|
| *Flower:* | | | | |
| Main body color of petals | | 50 | K | 4 |
| Darker shades on petals | Cerise | 4 | J | 6 |
| Occasional streaks; and section at very base of petals. | White | 1 | A | 1 |
| Group of pistils and stamens. | Gold-brown | 14 | F | 12 |
| *Buds:* | | | | |
| Calyx and outside of sepals. | Lettuce-green | 20 | L | 5 |
| Inside of sepals | | 20 | F | 4 |
| *Leaves:* | | | | |
| Young leaves | Calliste green | 19 | L | 6 |
| With veins outlined in dark green. | | | | |
| Main mature leaves | Brunswick green md. | 23 | C | 12 |
| *Stems:* | | | | |
| Main stems | Art green | 22 | L | 7 |
| Section of stems bearing blossoms has area just back of flowers. | Argus brown | 7 | A | 12 |
| *Thorns:* | | | | |
| Medium size but long | Etruscan | 7 | H | 12 |
| *Young leaf shoots* | Antique bronze | 14 | L | 10 |
| *Petals showing in unopened buds.* | Old red | 5 | K | 6 |

The blossoms are borne in clusters, as on the parent rose, on strong, upright stems. They are mildly fragrant and when cut with ordinary care do not wither on the stems for about two weeks.

The buds are also cup-shaped having 5 long, green sepals which "hood" above the buds and curl downwardly as the buds open. The tightly closed buds are an old red changing into a cerise upon unfolding.

As in the parent plant, the number of leaves gives a bushy effect. The thorns are hook-shaped, growing in staggered relation on the peduncle and gradually diminishing until they show as prickles on the pedicels.

The following is a detailed description of the rose plant and flower:

*Bloom*

*Parentage.*—Sport of Mrs. Finch

*Color.*—General appearance, cerise

*Size.*—About 2 inches wide and about 1 inch in depth

*Borne.*—In clusters like Mrs. Finch

*Form.*—More cup-shaped, more open and more double than Mrs. Finch

*Blooms.*—Continuously

*Lasting quality.*—Very good

*Bud*

*Form.*—Cup-shaped

*Size.*—Tightly closed bud about ½ inch in depth

*Color.*—Tightly closed bud old red, showing cerise when half open

*Foliage.*—Substantially the same as paren plant.

This new variety is distinguished from its par ent by its deeper pink, greater doubleness, mor open flower and longer keeping qualities.

I claim:

A new and distinct variety of rose, a sport fron "Mrs. Finch", similar thereto in habits of growth but distinguishable therefrom chiefly by its general warm, deep shade of cerise blossoms witl lighter touches of pink near the base of the petals its persistence in retaining this color, and by its profusion of blossoms, substantially as shown anc described.

FRED C. STIELOW.